(12) United States Patent
Ly et al.

(10) Patent No.: US 10,809,194 B2
(45) Date of Patent: Oct. 20, 2020

(54) SURFACE PLASMON RESONANCE IMAGING SYSTEM AND METHOD FOR MEASURING MOLECULAR INTERACTIONS

(71) Applicant: Biosensing Instrument Inc., Tempe, AZ (US)

(72) Inventors: Nguyen Ly, Tempe, AZ (US); Tianwei Jing, Tempe, AZ (US)

(73) Assignee: BIOSENSING INSTRUMENT INC., Tempe, AZ (US)

( * ) Notice: Subject to any disclaimer, the term of this patent is extended or adjusted under 35 U.S.C. 154(b) by 0 days.

(21) Appl. No.: 16/423,733

(22) Filed: May 28, 2019

(65) Prior Publication Data
US 2019/0360932 A1 Nov. 28, 2019

Related U.S. Application Data

(63) Continuation of application No. PCT/US2019/034087, filed on May 27, 2019.
(Continued)

(51) Int. Cl.
*G01N 21/552* (2014.01)
*G01N 21/59* (2006.01)

(52) U.S. Cl.
CPC ..... *G01N 21/553* (2013.01); *C12Q 2565/628* (2013.01); *G01N 2021/5903* (2013.01)

(58) Field of Classification Search
CPC .. C12G 2565/628; G01N 21/43; G01N 21/55; G01N 21/552; G01N 21/553;
(Continued)

(56) References Cited

U.S. PATENT DOCUMENTS 4,297,032 A * 10/1981 Temple ............... G01N 21/88
356/237.1
6,268,125 B1 * 7/2001 Perkins ............... G01N 21/553
435/5
(Continued)

FOREIGN PATENT DOCUMENTS

EP 2409153 5/2014
JP 2001255267 A * 9/2001 ........... G01N 21/253
(Continued)

OTHER PUBLICATIONS

Huang, Bo et al., "Surface Plasmon Resonance Imaging Using a High Numerical Aperture Microscope Objective," Apr. 1, 2007, Analytical Chemistry, vol. 79, No. 7, pp. 2979-2983. (Year: 2007).*
(Continued)

*Primary Examiner* — Gordon J Stock, Jr.
(74) *Attorney, Agent, or Firm* — Bryan Cave Leighton Paisner LLP (57) ABSTRACT

A system in an embodiment can comprise an optical assembly, an SPR light source, and an SPR camera. The optical assembly in this embodiment can comprise a hemispherical prism comprising a planar top surface configured to support a surface-plasmon-resonance (SPR) sensor; a high numerical aperture (NA) lens; and a housing configured to mount the hemispherical prism and the high NA lens the such that the high NA lens is located distal from the planar top surface of the hemispherical prism. The SPR light source in this embodiment can be configured to emit a low-coherent monochromatic light beam for SPR imaging toward the high NA lens. The SPR camera in this embodiment can be configured to capture an SPR image formed after the low-coherent monochromatic light beam is incident upon and reflected by a metal-coated sample contacting surface of the SPR sensor. Additionally, the high NA lens in this embodiment can be configured to refract the low-coherent mono-
(Continued)

chromatic light beam from the SPR light source toward the hemispherical prism; and the hemispherical prism can be configured to collimate the low-coherent monochromatic light beam, as refracted by the high NA lens, toward the SPR sensor. Other embodiments are disclosed.

22 Claims, 11 Drawing Sheets

Related U.S. Application Data (60) Provisional application No. 62/676,983, filed on May 27, 2018.

(58) Field of Classification Search
CPC ............... G01N 21/554; G01N 21/59; G01N 2021/434; G01N 2021/435; G01N 2021/436; G01N 2021/437; G01N 2021/438; G01N 2021/5903
See application file for complete search history.

(56) References Cited

U.S. PATENT DOCUMENTS

| | | | |
|---|---|---|---|
| 6,579,726 B1 | 6/2003 | Natan et al. | |
| 6,753,188 B2* | 6/2004 | Perkins | G01N 21/553 436/172 |
| 6,849,397 B2 | 2/2005 | Nelson et al. | |
| 7,030,989 B2 | 4/2006 | Yager et al. | |
| 7,670,556 B2 | 3/2010 | Corn et al. | |
| 7,751,052 B2 | 7/2010 | Pyo et al. | |
| 7,957,058 B2* | 6/2011 | Sugiura | G02B 21/082 359/368 |
| 8,802,410 B2 | 8/2014 | Käck et al. | |
| 8,982,353 B2 | 3/2015 | Masson et al. | |
| 2005/0048599 A1 | 3/2005 | Goldberg et al. | |
| 2005/0159657 A1* | 7/2005 | Cappo | G01N 21/553 600/315 |
| 2006/0134669 A1 | 6/2006 | Casasanta, III | |
| 2006/0170918 A1* | 8/2006 | Nishiuma | G01N 21/553 356/318 |
| 2007/0081163 A1 | 4/2007 | Liang et al. | |
| 2009/0027680 A1 | 1/2009 | Furusawa | |
| 2009/0213382 A1* | 8/2009 | Tracy | G01N 21/253 356/445 |
| 2009/0262356 A1* | 10/2009 | Boeschoten | G01N 21/253 356/445 |
| 2010/0271632 A1* | 10/2010 | Johansen | B82Y 20/00 356/445 |
| 2010/0284013 A1 | 11/2010 | Iwasaki et al. | |
| 2010/0285612 A1* | 11/2010 | Iwasaki | G01F 1/704 436/518 |
| 2010/0311103 A1 | 12/2010 | Boukherroub et al. | |
| 2011/0216320 A1 | 9/2011 | Cho et al. | |
| 2011/0310383 A1 | 12/2011 | Masson et al. | |
| 2012/0154814 A1* | 6/2012 | Zare | G01N 21/553 356/445 |
| 2013/0240734 A1 | 9/2013 | Booksh et al. | |
| 2014/0185051 A1* | 7/2014 | Guan | G01N 21/553 356/445 |
| 2014/0363823 A1 | 12/2014 | Goldberg et al. | |
| 2014/0371093 A1 | 12/2014 | Mercey | |
| 2015/0168300 A1 | 6/2015 | Peterson et al. | |
| 2016/0299069 A1* | 10/2016 | Tao | G01N 21/553 |
| 2017/0052133 A1 | 2/2017 | Opdahl | |
| 2017/0336612 A1* | 11/2017 | Foley, IV | G02B 21/0092 |
| 2018/0246089 A1 | 8/2018 | Chou et al. | |
| 2018/0321150 A1* | 11/2018 | Gavaris | G01N 21/554 |
| 2018/0372634 A1 | 12/2018 | Krishnamoorthy et al. | |

FOREIGN PATENT DOCUMENTS

| | | |
|---|---|---|
| KR | 20100109020 | 10/2010 |
| WO | 2001035081 | 5/2001 |
| WO | 2009074660 | 6/2009 |
| WO | 2012070942 | 5/2012 |

OTHER PUBLICATIONS

Lokate, Angelique M.C. et al., "Biomolecular Interaction Monitoring of Autoantibodies by Scanning Surface Plasmon Resonance Microarray Imaging," 2007, Journal of the American Chemical Society, 129, pp. 14013-14018. (Year: 2007).*
International Search Report and Written Opinion for International Application No. PCT/US2019/034087, dated Sep. 18, 2019.
Giebel, et al., "Imaging of Cell/Substrate Contacts of Living Cells with Surface Plasmon Resonance Microscopy," Biophysical Journal, vol. 76, pp. 509-516, Jan. 1999.
Guan, et al., "Kinetics of Small Molecule Interactions with Membrane Proteins in Single Cells Measured with Mechanical Amplification," Sci. Adv. 2015;1:e1500633, Oct. 23, 2015.
Hide, et al., "Real-Time Analysis of Ligand-Induced Cell Surface and Intracellular Reactions of Living Mast Cells Using a Surface Plasmon Resonance-Based Biosensor," Analytical Biochemistry 302, pp. 28-37, Jan. 23, 2002.
Peterson, et al., "Surface Plasmon Resonance Imaging of Cells and Surface-Associated Fibronectin," BMC Cell Biology 2009, 10:16, Feb. 26, 2009.
Thiel, et al., "In Situ Surface Plasmon Resonance Imaging Detection of DNA Hybridization to Oligonucleotide Arrays on Gold Surfaces," Analytical Chemistry, vol. 69, No. 24, pp. 4948-4956, Dec. 15, 1997.
Wang, et al., "Label-Free Measuring and Mapping of Binding Kinetics of Membrane Proteins in Single Living Cells," Nature Chemistry 4, pp. 846-853, Aug. 26, 2012.
Yang, et al., "Interferometric Plasmonic Imaging and Detection of Single Exosomes," PNAS, vol. 115, No. 41, pp. 10275-10280, Oct. 9, 2018.
Zhang, et al., "Label-Free Quantification of Small-Molecule Binding to Membrane Proteins on Single Cells by Tracking Nanometer-Scale Cellular Membrane Deformation," ACS Nano, vol. 12, pp. 2056-2064, 2018.
Ziblat, et al., "Infrared Surface Plasmon Resonance: A Novel Tool for Real Time Sensing of Variations in Living Cells," Biophysical Journal, vol. 90, pp. 2592-2599, Apr. 2006.

* cited by examiner

SURFACE PLASMON RESONANCE IMAGING SYSTEM AND METHOD FOR MEASURING MOLECULAR INTERACTIONS

CROSS-REFERENCE TO RELATED APPLICATIONS

This application is a continuation of, and claims priority to PCT/US19/34087, filed May 27, 2019. PCT/US19/34087 claims priority to U.S. Provisional Patent Application No. 62/676,983, filed May 27, 2018. U.S. Provisional Patent Application No. 62/676,983 is incorporated herein by reference in its entirety.

TECHNICAL FIELD

This disclosure relates generally to surface plasmon resonance (SPR) imaging systems, and methods to use such systems, for measuring molecular interactions.

BACKGROUND

Surface plasmon resonance (SPR) detection using incident light beam is a popular technique for monitoring molecular interactions in real-time. However, traditional SPR devices or systems are not suitable for the study of heterogeneity effects naturally occurred in cell population because they either have limited fields of view or are not design for imaging cellular structures or phenotypes that often have random patterns and structures. Therefore, systems and methods configured to have a large field of view and a high resolution for measuring molecular interactions in real time are desired.

BRIEF DESCRIPTION OF THE DRAWINGS

To facilitate further description of the embodiments, the following drawings are provided in which.

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

The terms "couple," "coupled," "couples," "coupling," and the like should be broadly understood and refer to connecting two or more elements mechanically and/or otherwise. Two or more electrical elements may be electrically coupled together, but not be mechanically or otherwise coupled together. Coupling may be for any length of time, e.g., permanent or semi-permanent or only for an instant. "Electrical coupling" and the like should be broadly understood and include electrical coupling of all types. The absence of the word "removably," "removable," and the like near the word "coupled," and the like does not mean that the coupling, etc. in question is or is not removable.

As defined herein, two or more elements are "integral" if they are comprised of the same piece of material. As defined herein, two or more elements are "non-integral" if each is comprised of a different piece of material.

As defined herein, "approximately" can, in some embodiments, mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

As defined herein, "real-time" can, in some embodiments, be defined with respect to operations carried out as soon as practically possible upon occurrence of a triggering event. A triggering event can include receipt of data necessary to execute a task or to otherwise process information. Because of delays inherent in transmission and/or in computing speeds, the term "real time" encompasses operations that occur in "near" real time or somewhat delayed from a triggering event. In a number of embodiments, "real time" can mean real time less a time delay for processing (e.g., determining) and/or transmitting data. The particular time delay can vary depending on the type and/or amount of the data, the processing speeds of the hardware, the transmission capability of the communication hardware, the transmission distance, etc. However, in many embodiments, the time delay can be less than approximately one second, five seconds, ten seconds, thirty seconds, one minute, five minutes, ten minutes, or fifteen minutes.

DESCRIPTION OF EXAMPLES OF EMBODIMENTS

Turning to the drawings, FIGS. 1-5 illustrate various views of an SPR imaging system 100, according to an embodiment. In this and other embodiments, the SPR imaging system 100 can comprise: (a) an optical assembly 110; (b) an SPR light source 120; (c) an SPR camera 130; (d) a bright field light source 140; and/or (e) a bright field camera 150. In many embodiments, the SPR imaging system 100 can comprise a high optical resolution, such as an optical resolution not larger than 3 micrometers (µm), 2 µm, etc. In these and other embodiments, the SPR imaging system 100 also can comprise a wide SPR angle, such as an SPR angle ranging from 40 to 82 degrees. In some embodiments, the SPR imaging system 100 can further comprise a large optical field of view, such as an optical field of view as great as 0.1 millimeters-squared ($mm^2$), 1 $mm^2$, or 3 $mm^2$. In many embodiments, the SPR imaging system 100 can be configured to simultaneously capture or process an SPR image and a bright field image in real time.

In many embodiments, the optical assembly 110 of the SPR imaging system 100 can comprise: (a) a hemispherical prism 112 that comprises a planar top surface 113 configured to support a surface-plasmon-resonance (SPR) sensor 170; (b) a high numerical aperture (NA) lens 114; and/or (c) a housing 116 configured to mount the hemispherical prism 112 and the high NA lens 114, such that the high NA lens 114 is located distal from the planar top surface 113 of the hemispherical prism 112. In some embodiments, the top surface of the hemispherical prism is not planar or is not entirely planar.

In many embodiments, with the hemispherical prism 112 configured to support the SPR sensor 170, no sensor supporting stage is needed, and the SPR imaging system 100 thus can have fewer heat leaking surfaces and fewer sources of mechanical vibration noise. In many embodiments, the hemispherical prism 112 can comprise a high refractive index, such as a refractive index no less than 1.5. In these and other embodiments, the high NA lens 114 can comprise a radius at least 1.5 times greater than a radius of the hemispherical prism 112. In some embodiments, the high NA lens 114 can comprise a high NA value, such as no less than 1.5.

In many embodiments where optical assembly 110 of the SPR imaging system 100 comprises the housing 116, the hemispherical prism 112 and the high NA lens 114 can be configured to be firmly coupled to the housing 116 in order to eliminate any relative movement between the hemispherical prism 112 and the high NA lens 114 that can cause mechanical vibration noises. In these and other embodiments, the housing 116 can enclose at least a portion of each of the hemispherical prism 112 and the high NA lens 114 for better temperature control. In one such embodiment, the housing 116 can enclose the area between the hemispherical prism 112 and the high NA lens 114. In the same or different embodiment, the housing 116 can leave the planar top surface 113 of the hemispherical prism 112 and the bottom surface of the high NA lens exposed, as in the exemplary embodiment shown in FIGS. 1 and 3.

In many embodiments, the SPR light source 120 of the SPR imaging system 100 can be configured to emit a low-coherent monochromatic light beam 121 for SPR imaging toward the high NA lens 114. In many embodiments, an incident angle of the low-coherent monochromatic light beam 121 from the SPR light source 120 towards the high NA lens 114 can be adjustable, such as by one or more additional optical components or by adjusting the location or angle of the SPR light source 120. In many embodiments, the SPR camera 130 can be configured to capture an SPR image formed after the low-coherent monochromatic light beam 121 is incident upon and reflected by a metal-coated sample contacting surface 171 of the SPR sensor 170.

In many embodiments, the SPR imaging system 100 can comprise the bright field light source 140 and the bright field camera 150 for bright field imaging. In many embodiments, the bright field light source 140 can be configured to emit a bright field light beam 141 to illuminate the metal-coated sample contacting surface 171 of the SPR sensor 170, and the bright field camera 150 can be configured to capture a bright field image of the SPR sensor 170. In some and other embodiments, the bright field light source 140 can additionally comprise a condenser. As an example, the condenser can be configured to render a light beam, that is emitted from the bright field light source 140 and originally divergent, into a parallel and/or convergent bright field light beam to illuminate the SPR sensor 170. In many embodiments, the SPR imaging system 100 can be configured so that the bright field camera 150 can capture the bright field image of the SPR sensor 170 simultaneously with the SPR camera capturing the SPR image.

In many embodiments, the high NA lens 114 can be configured to refract the low-coherent monochromatic light beam 121 from the SPR light source 120 toward the hemispherical prism 112. In the same or different embodiments, the high NA lens 114 can condition the low-coherent monochromatic light beam 121 or 122. As an example, the conditioning provided by the high NA lens 114 can bend the refracting beam, 121 or 122, 30-60 degrees from incident beam path, for both beams 121 and 122 towards and away from the sensor 170. In many embodiments, the hemispherical prism 112 can be configured to collimate the low-coherent monochromatic light beam 121, as refracted by the high NA lens 114, toward the SPR sensor 170 that is coupled to the planar top surface 113 of the hemispherical prism 112.

In many embodiments, the SPR camera 130 and/or the bright field camera 150 can be communicably coupled to a computing device 180 (FIG. 1), such as a computer or a server, that is configured to: receive and record the SPR image from the SPR camera; receive and record the bright field image from the bright field camera; calibrate the SPR image from the SPR camera; calibrate the bright field image from the bright field camera; and map the SPR image onto the bright field image for binding analysis. In some embodiments, the computing device 180 (FIG. 1) can be further configured to automatically perform one or more data processing procedures, including: (a) normalizing the SPR sensitivity of the sensor surface per pixel and removing the sensor inhomogeneity by one or more calibration techniques, such as an SPR profile scan, injection of a known index standard, a thermal response, or another known method to determine localized SPR sensor sensitivity; (b) removing sensor drift by leveling the baseline with reference, linear, and non-linear subtractions; (c) identifying anomalous data of binding behaviors and eliminating artifacts in the data by using Artificial Intelligence ("AI") to categorize binding behaviors and exclude the data which do not match between isotherm analysis and kinetic analysis; and/or (d) identifying one or more sets of data showing model behaviors as the model data and analyzing the model data to derive a measured result with a certain confidence level.

Furthermore, in many embodiments, the SPR imaging system 100 can comprise additional optical components, such as one or more lenses, one or more mirrors, a phase-shift ring 161 (FIG. 4), and/or a color filter 162 (FIG. 5), and so forth, for adjusting the colors or directions of the light beams and/or the colors or contrast of the bright field image or the SPR image for SPR imaging, bright field imaging, phase-contrast imaging, and/or fluorescence imaging. For instance, in some embodiments, the phase-shift ring 161 can be configured for phase-contrast imaging with the bright field light source 140 and the bright field camera 150 to increase the contrast of the bright field image, and the phase-shift ring 161 can be located in any suitable place, such as between the hemispherical prism 112 and the high NA lens 114 or between the optical assembly 110 and the bright field camera 150. In many embodiments, the bright field light source 140 and the bright field camera 150 can be further configured for fluorescence imaging with one of: (a) the bright field light beam 141 (see also, 341 (FIG. 7)) emitted by the bright field light source 140 comprising a colored light; or (b) the bright field light beam 141 emitted by the bright field light source 140 comprising a white light and the color filter 162 located at one of: between the bright field light source 140 and the SPR sensor 170 or in front of bright field camera 150, and configured to change one or more colors of bright field light beam 141/142 (see also, 341/342 (FIG. 7)).

Figure 1:
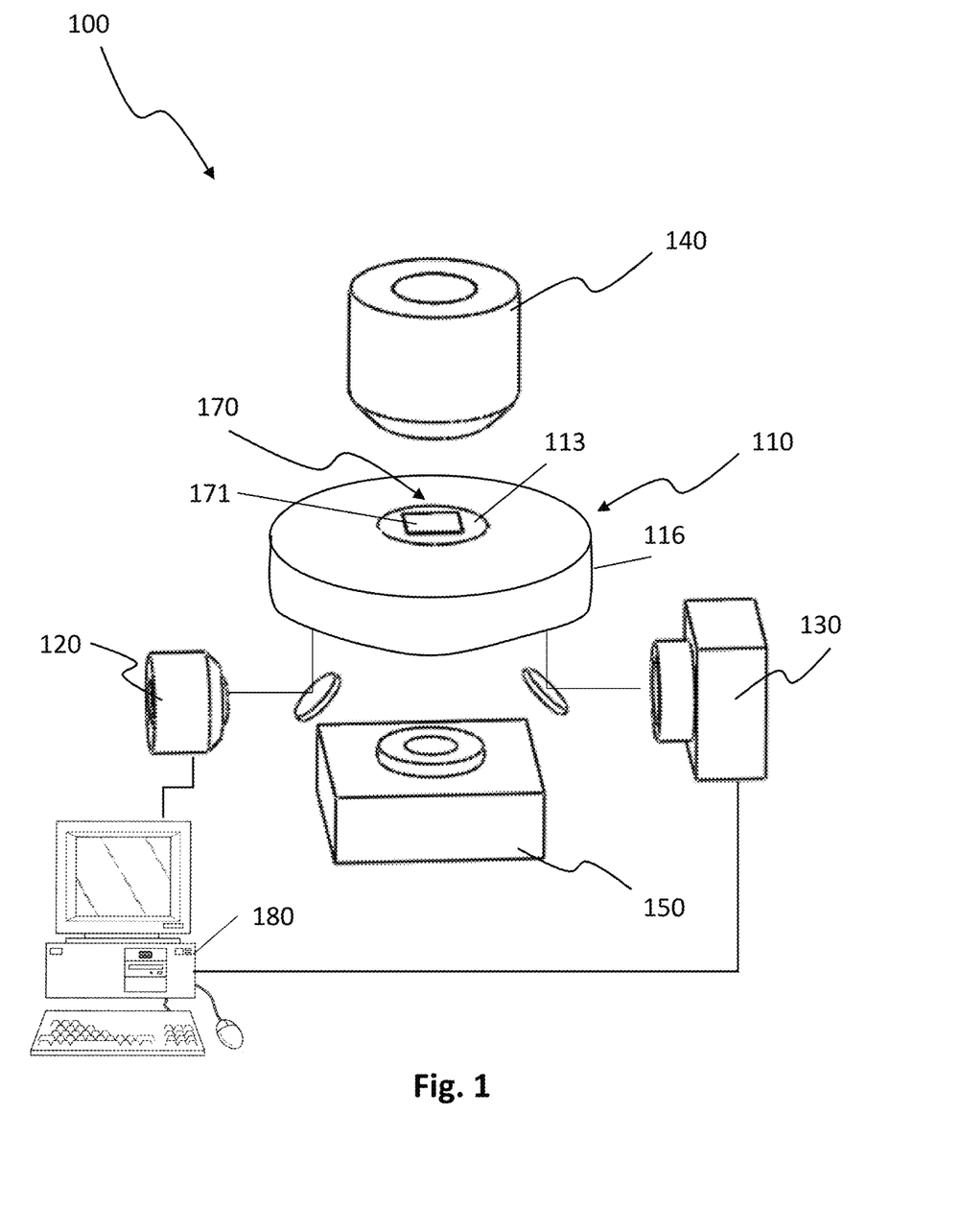
FIG. 1 illustrates a perspective view of an SPR imaging system, according to an embodiment.
Figure 2:
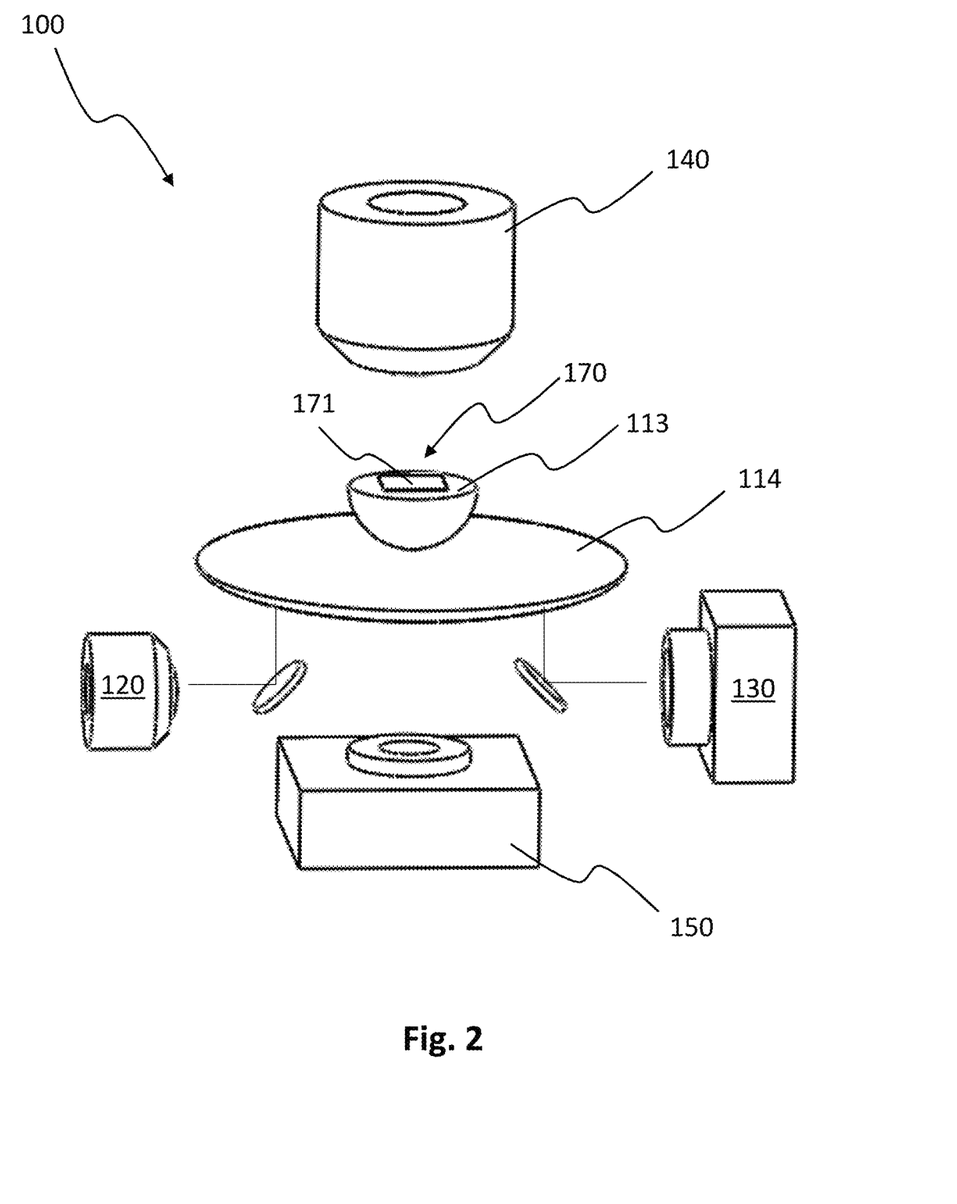
FIG. 2 shows a perspective view of the SPR imaging system, according to the embodiment in FIG. 1, in which the housing of an optical assembly is omitted.
Figure 3:
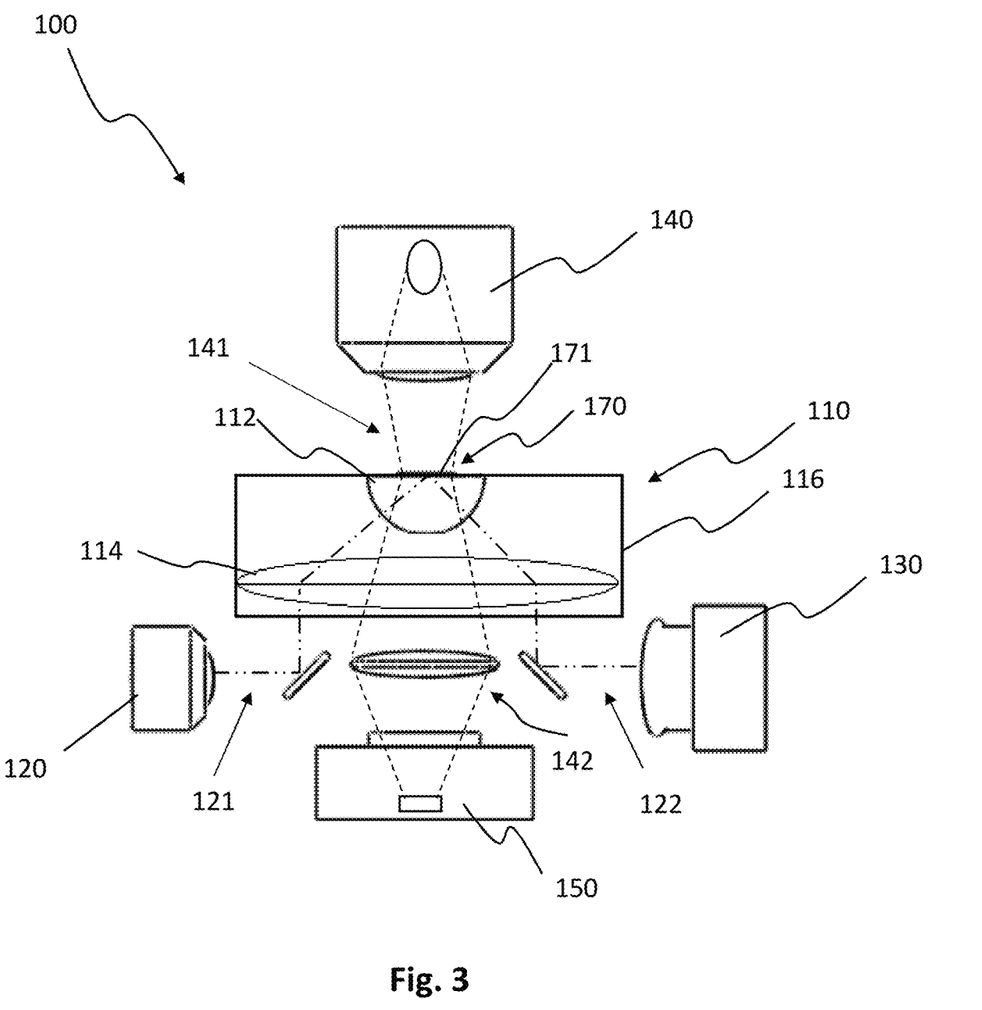
FIG. 3 shows a side elevational view of the SPR imaging system with the housing of the optical assembly cut open, according to the embodiment in FIG. 1.
Figure 4:
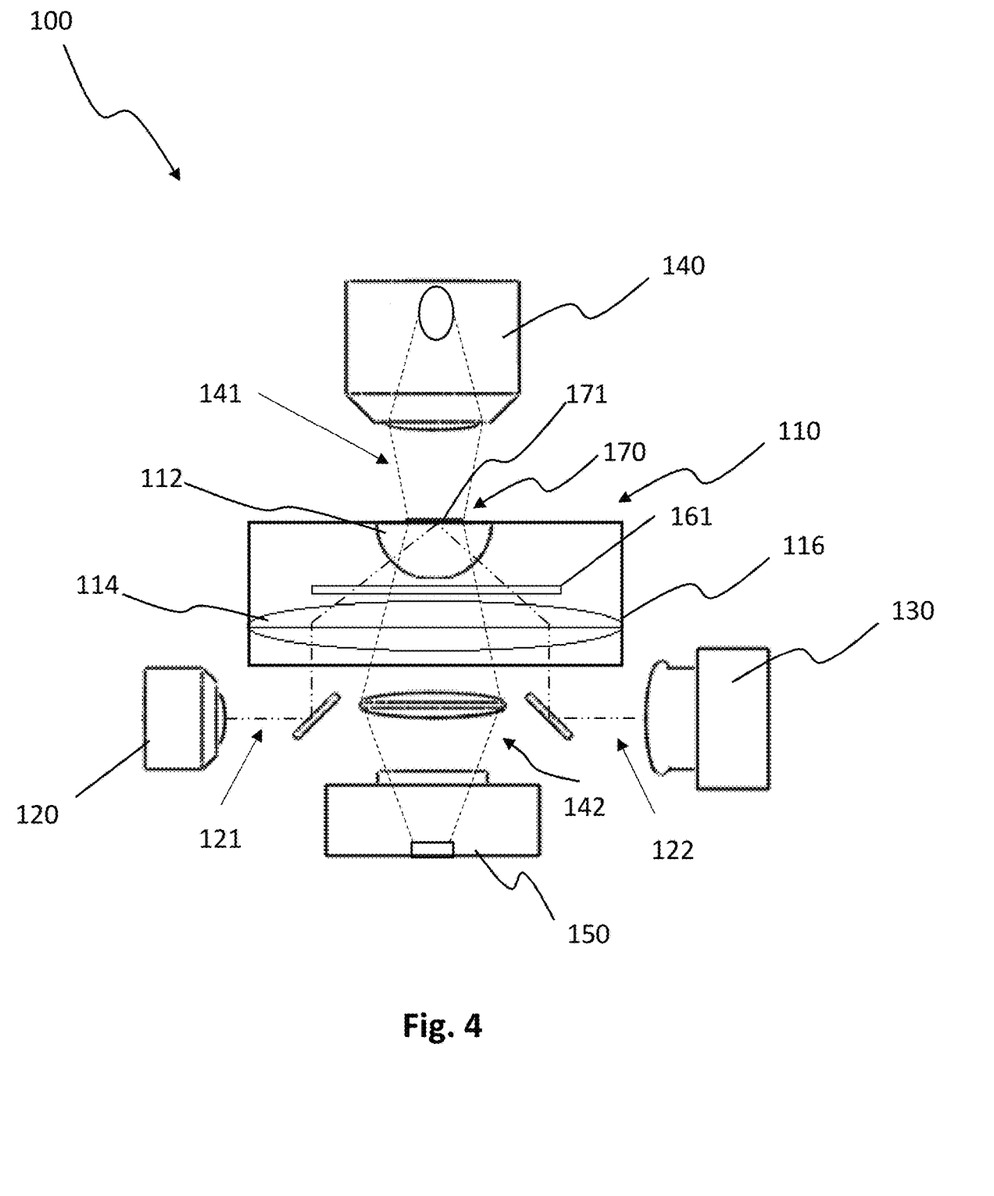
FIG. 4 shows side elevational view of the SPR imaging system with a phase-shift filter, according to the embodiment in FIG. 3.
Figure 5:
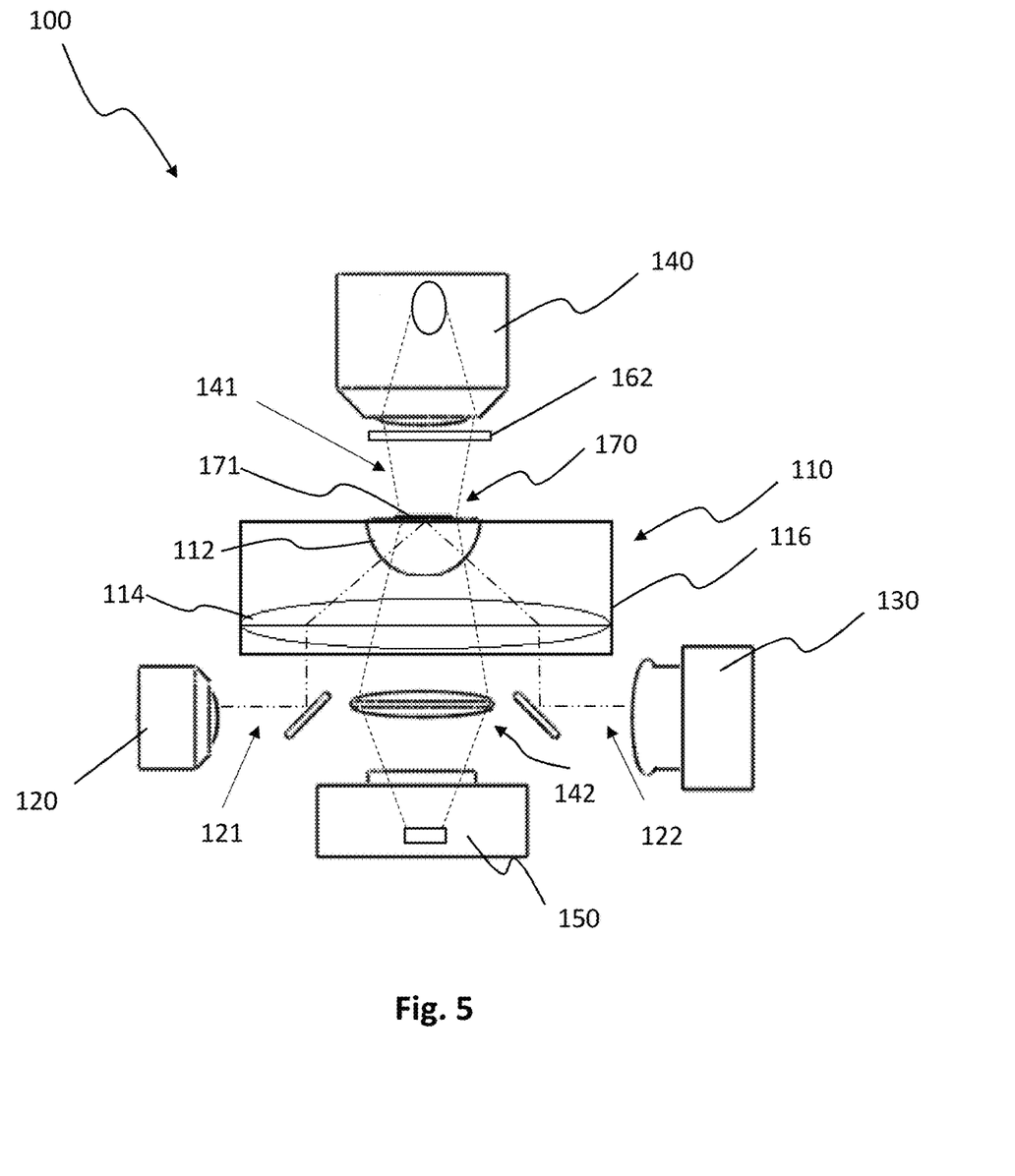
FIG. 5 shows side elevational view of the SPR imaging system with a color filter, according to the embodiment in FIG. 3.
Figure 6:
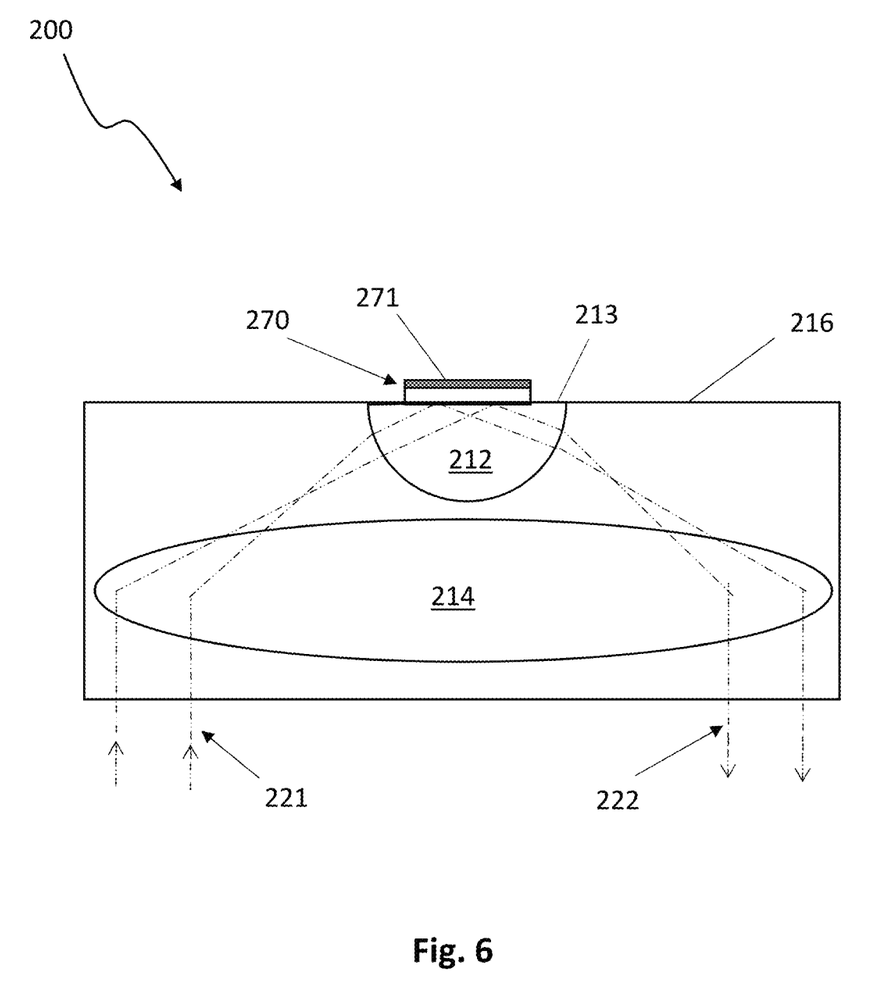
FIG. 6 illustrates a cross sectional view of an optical assembly, according to another embodiment.

Turning to the drawings, FIG. 6 illustrates an optical assembly 200, according to an embodiment. In many embodiments, the optical assembly 200 can comprise a hemispherical prism 212, a high NA lens 214, and/or a housing 216. In many embodiments, the hemispherical prism 212 can comprise a planar top surface 213 configured to support an SPR sensor 270 with a metal-coated sample contacting surface 271. In some embodiments, the top surface of the hemispherical prism is not planar or is not entirely planar. In many embodiments, the housing 216 can be configured to mount the hemispherical prism 212 and the high NA lens 214, such that the high NA lens 214 is located distal from the planar top surface 213 of the hemispherical prism 212. In many embodiments, an SPR imaging system adopting the optical assembly 200 can comprise: a high optical resolution, such as an optical resolution not larger than 3 μm, 1 μm, etc.; a wide SPR angle, such as an SPR angle ranging from 40 to 82 degrees; and/or a large optical field of view, such as an optical field of view as great as 0.1 mm², 1 mm², or 3 mm². In many embodiments, the optical assembly 200 can be used for simultaneous SPR and bright field imaging.

In many embodiments, the hemispherical prism 212 can comprise a high refractive index, such as a refractive index no less than 1.5. In these and other embodiments, the high NA lens 214 can comprise a radius at least 1.5 times greater than a radius of the hemispherical prism 212. In some embodiments, the high NA lens 214 can comprise a high NA value, such as no less than 1.5. In many embodiments, the hemispherical prism 212 and the high NA lens 214 can be configured to be firmly coupled to the housing 216 in order to eliminate any relative movement between the hemispherical prism 212 and the high NA lens 214 that can cause mechanical vibration noise. In these and other embodiments, the housing 216 can enclose at least a portion of each of the hemispherical prism 212 and the high NA lens 114 for better temperature control, such as enclosing the area between the hemispherical prism 212 and the high NA lens 214.

Figure 7:
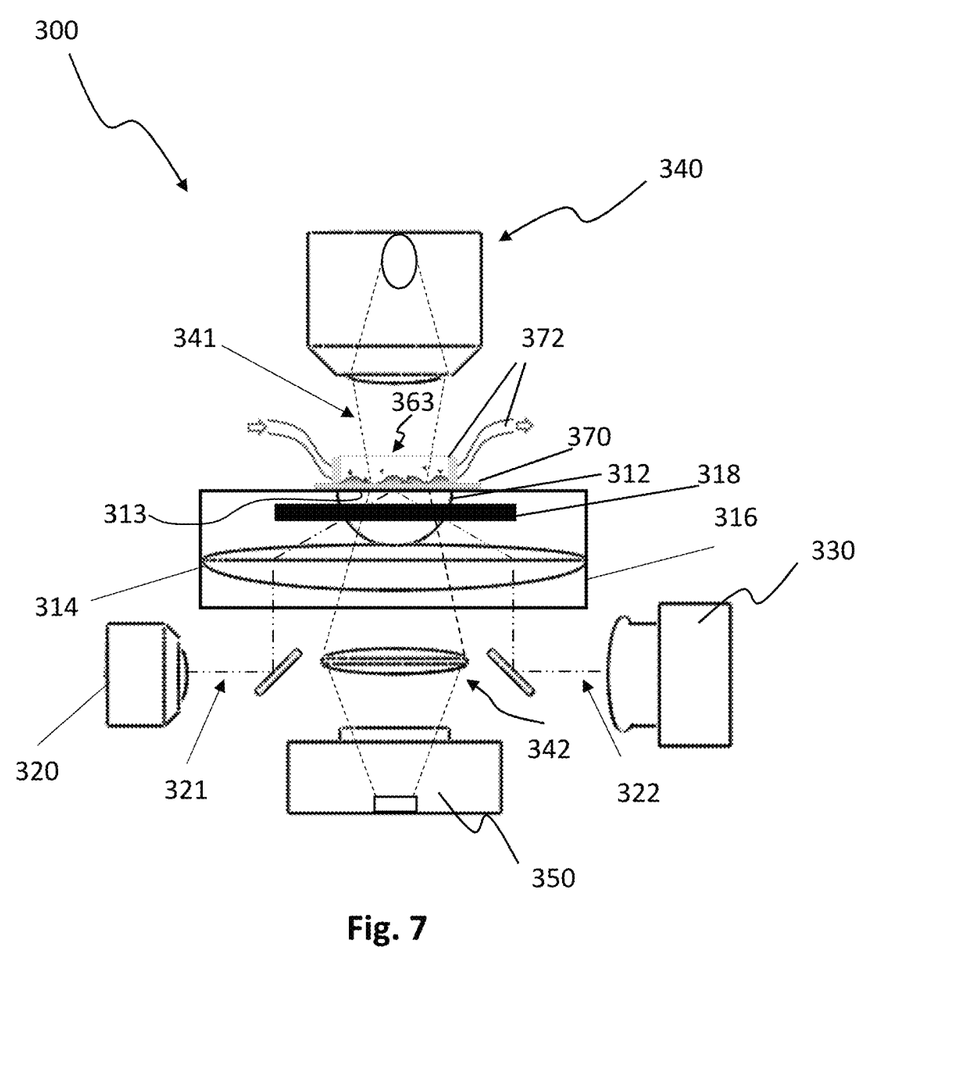
FIG. 7 shows a side elevational view of an SPR imaging system, according to another embodiment.
Figure 8:
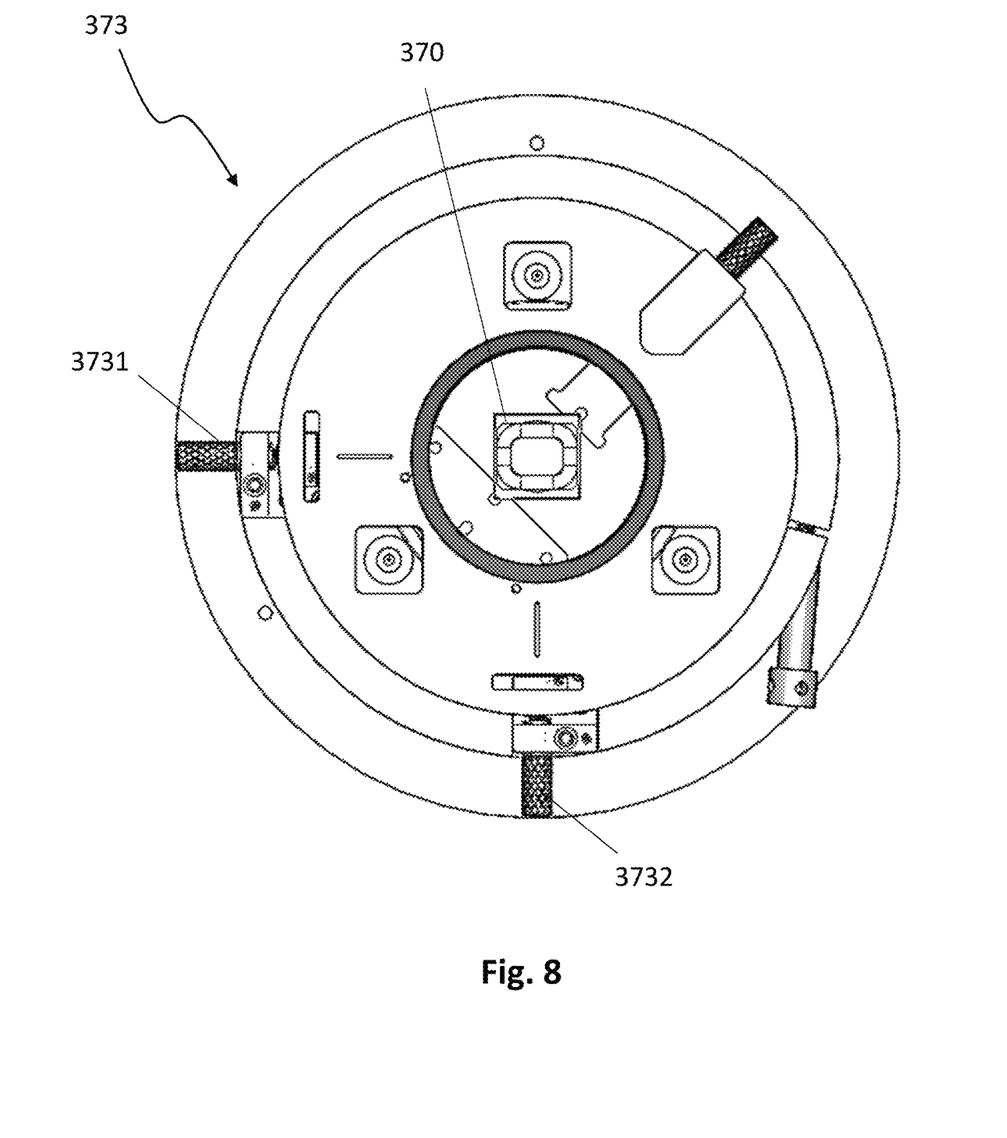
FIG. 8 shows a top plain view of a sensor translation mount and an SPR sensor of the SPR imaging system, according to the embodiment in FIG. 7.
Figure 9:
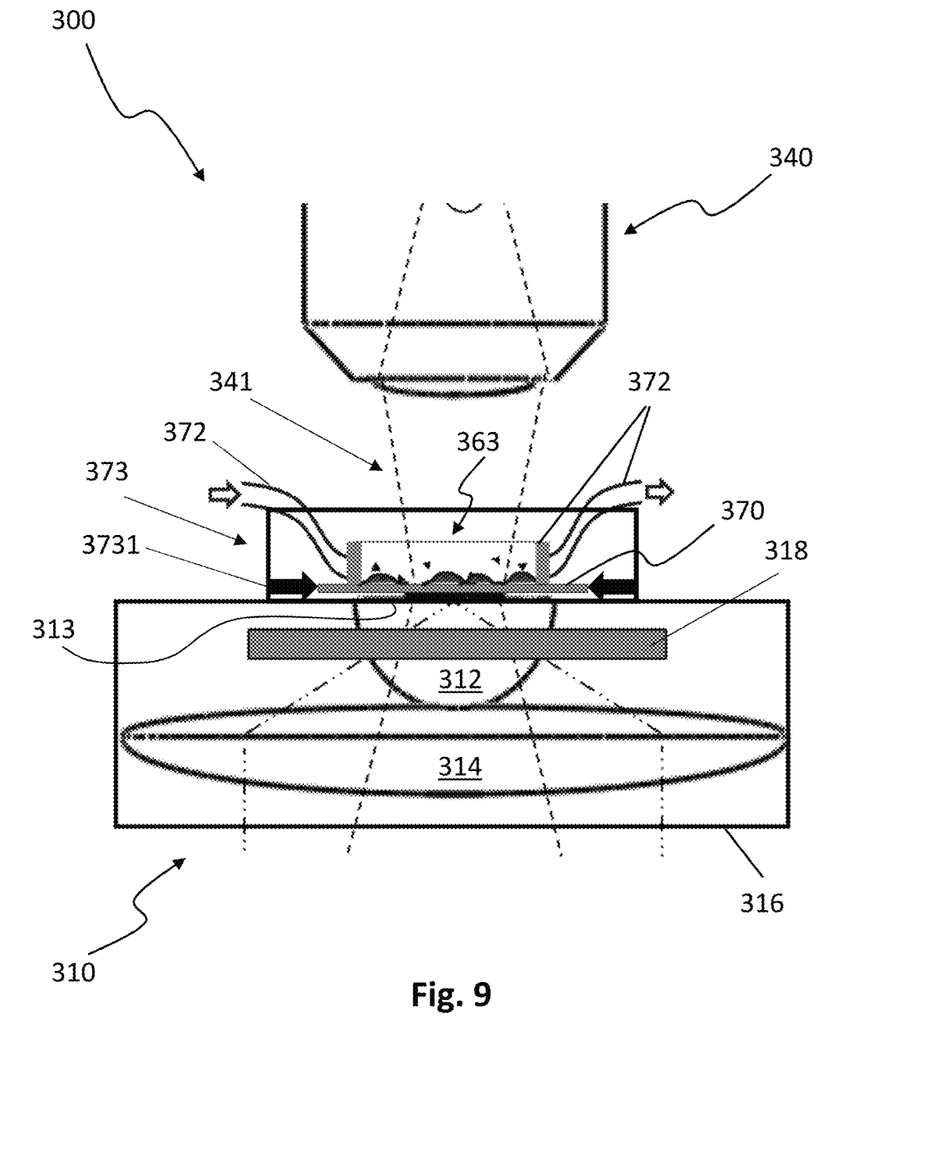
FIG. 9 shows a partial enlarged view of the SPR imaging system, according the embodiment in FIG. 7.

Turning to the drawings, FIGS. 7-9 illustrate various views of an SPR imaging system 300, according to another embodiment. In this and other embodiments, the SPR imaging system 300 can comprise: (a) an optical assembly 310; (b) an SPR light source 320; (c) an SPR camera 330; (d) a bright field light source 340; (e) a bright field camera 350; (f) a thermoelectric device 318; (g) a microfluidic device 372; and/or (h) a sensor translation mount 373 (FIGS. 8-9). In many embodiments, the optical assembly 310 can comprise a hemispherical prism 312, a high NA lens 314, a thermoelectric device 318, and/or a housing 316. In many embodiments, the hemispherical prism 312, the high NA lens 314, and the housing 316 can be similar to the aforementioned hemispherical prism (112 (FIG. 1-5) or 212 (FIG. 6)), the high NA lens (114 (FIG. 1-5) or 214 (FIG. 6)), and/or the housing (116 (FIG. 1-5) or 216 (FIG. 6)), respectively.

In many embodiments, the thermoelectric device 318 can be configured to control the temperature of the SPR sensor 370, such as maintaining the temperature fluctuation of the SPR sensor 370 within 0.016 degrees Celsius (° C.), in order to avoid noises such as baseline shift in the SPR response signal or change in SPR angle. In some embodiments, the thermoelectric device 318 can be located within the optical assembly 310, such as near the top surface of the hemispherical prism 312, and/or partially or entirely surrounding the hemispherical prism 312, in order to maintain the temperature of the hemispherical prism 312 and, in turn, maintain the temperature of the SPR sensor 370.

In many embodiments, the microfluidic device 372 can be mountable on the SPR sensor 370 and configured to deliver a buffer solution with one or more ligand samples 363 onto the metal-coated sample contacting surface of the SPR sensor 370. In some embodiments, the microfluidic device 372 also can comprise: a pump with buffer exchange and degas capability configured to control a flow of the buffer solution; and/or an auto-sampler configured to place one or more ligand samples onto the metal-coated sample contacting surface of the SPR sensor 370.

In many embodiments, the SPR imaging system 300 can comprise the sensor translation mount 373 to monitor more cell population on a single SPR sensor 370. In many embodiments, the sensor translation mount 373 can be mountable on a planar top surface 313 of the hemispherical prism 312 and configured to hold the SPR sensor 370 and translate or move the SPR sensor 370, by an x adjust arm 3731 (FIGS. 8-9) and a y adjust arm 3732 (FIG. 8), on the planar top surface 313 of hemispherical prism 312, e.g., within a few millimeters on the planar top surface 313, to expand the measuring area on the SPR sensor 370, such as a measuring area as much as 4 times the area of the optical field of view of the SPR sensor 370. In many embodiments, a thin layer of matching oil (not shown) also can be applied between the SPR sensor 370 and the planar top surface 313 of the hemispherical prism 312 to eliminate any interface effect and provide lubricant for sensor translation. In some embodiments, the top surface of the hemispherical prism 312 is not planar or is not entirely planar.

Figure 10:
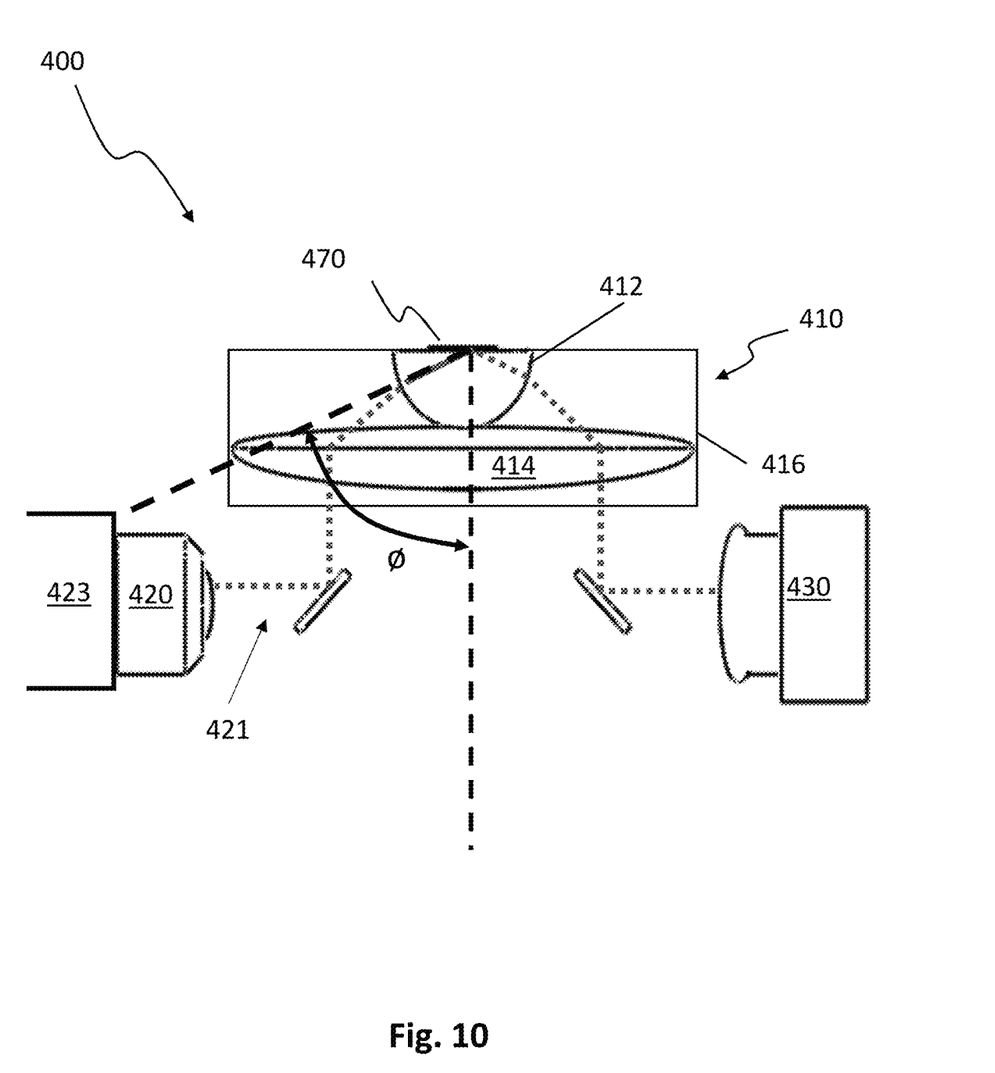
FIG. 10 shows a side elevational view of an SPR imaging system with the housing of the optical assembly cut open, according to an embodiment.
Figure 11:
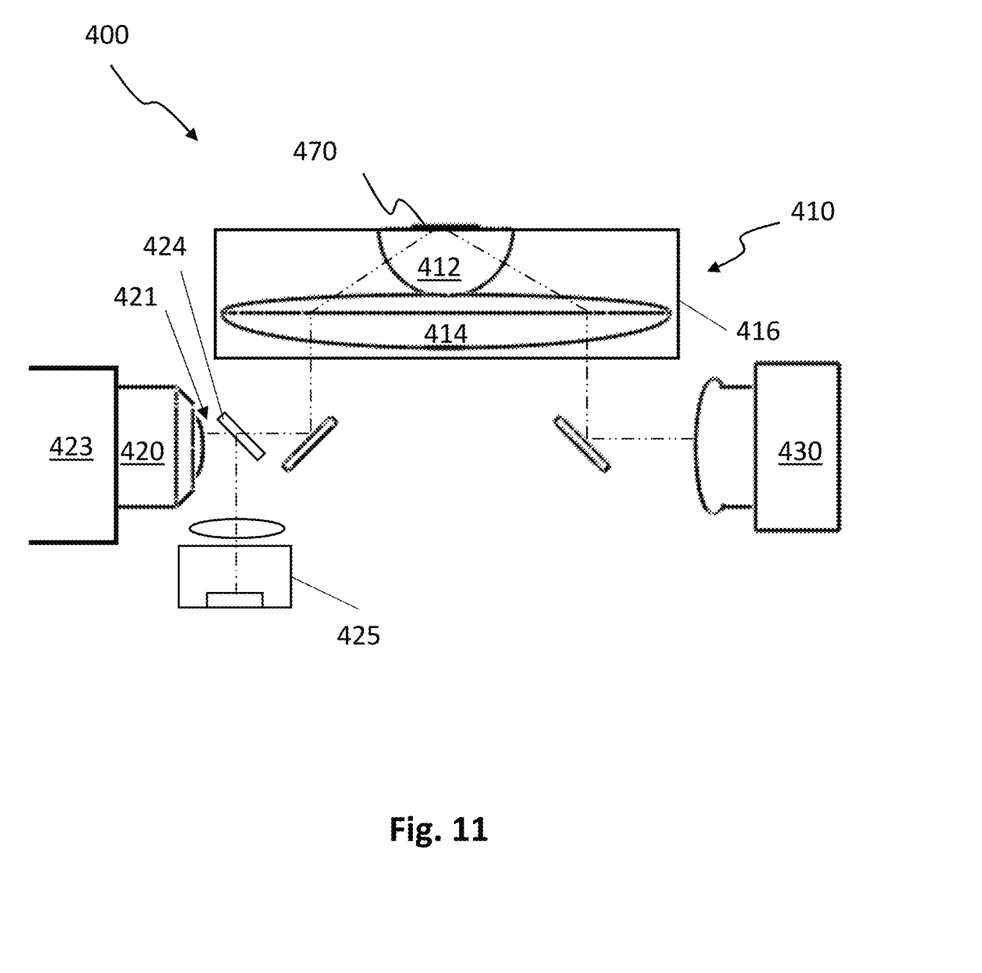
FIG. 11 shows a side elevational view of the SPR imaging system with a beam splitter and a light intensity detector, according to the embodiment in FIG. 10.

Turning to the drawings, FIGS. 10-11 show an SPR imaging system 400, according to an embodiment. In many embodiments, the SPR imaging system 400 can comprise a motorized frame 423 configured to change an incident angle θ of a low-coherent monochromatic light beam 421 relative to an optical assembly 410. As known in the art, a typical intensity-angle profile curve comprises a dip at the SPR angle, and an angle spread between the two steep slope regions near the dip is where a small angle shift can cause significant change in an intensity of SPR light shown in an SPR image; thus, measuring at the angle spread provides the highest sensitivity for SPR measurement. In many embodiments, the SPR imaging system 400 can be configured to automatically scan and/or adjust the angle θ of an incident low-coherent monochromatic light beam 421 to provide a wide range of angle adjustment, e.g., 40-82 degrees. The angle adjustment allows the detector to optimize the sensitivity in SPR measurement. For instance, in some embodiments, the motorized frame 423 configured can be configured to move the SPR light source 420 vertically or in one linear direction only to adjust the light path and then the incident angle θ of the low-coherent monochromatic light beam 421.

Additionally, as known in the art, the stability of an SPR light source, such as an SPR light source 420, can have a significant effect on SPR response signal measurement, and the measured reflectivity intensity $I_m$ is proportional to the incident light intensity $I_0$ times a function $\alpha(n)$ of sensor surface property and refractive index at and/or near its surface. That is, $I_m = \alpha(n) \times I_0$. To minimize this dependency of $I_0$, a normalized SPR signal $I_{spr}$ can be used:

$$I_{spr} = I_m/I_0 = \alpha(n), \text{ independent of } I_0.$$

Therefore, in many embodiments, the SPR imaging system 400 can further comprise a light intensity detector 425 (FIG. 11) configured to monitor and record the intensity of the low-coherent monochromatic light beam 421 for intensity normalization and noise reduction. In these and other embodiments, the SPR imaging system 400 also can comprise a beam splitter 424 (FIG. 11), such as a 50% beam splitter, located in the light path of incident low-coherent monochromatic light beam 421 to split the incident low-coherent monochromatic light beam 421 into two portions. In many embodiments, with the light intensity detector 425 and/or the beam splitter 424, the SPR imaging system 400 can be configured to automatically detect and/or maintain the intensity of the low-coherent monochromatic light beam 421.

In an embodiment, a system can comprise an optical assembly (e.g., 110 (FIGS. 1-5), 200 (FIG. 6), 310 (FIG. 9), or 410 (FIGS. 10-11)), an SPR light source (e.g., 120 (FIGS. 1-5), 320 (FIG. 7), or 420 (FIGS. 10-11)), and/or an SPR camera (e.g., 130 (FIGS. 1-5), 330 (FIG. 7), or 430 (FIGS. 10-11)). The optical assembly in this and other embodiments can comprise a hemispherical prism (e.g., 112 (FIGS. 1-5), 212 (FIG. 6), 312 (FIGS. 7 & 9), or 412 (FIGS. 10-11)) that comprises a top surface configured to support a surface-plasmon-resonance (SPR) sensor (e.g., 170 (FIGS. 1-5), 270 (FIG. 6), 370 (FIG. 7-9), or 470 (FIGS. 10-11)); a high numerical aperture (NA) lens (e.g., 114 (FIGS. 1-5), 214 (FIG. 6), 314 (FIGS. 7 & 9), or 414 (FIGS. 10-11)); and a housing (e.g., 116 (FIGS. 1-5), 216 (FIG. 6), 316 (FIGS. 7 & 9), or 416 (FIGS. 10-11)) configured to mount the hemispherical prism and the high NA lens such that the high NA lens is located distal from the top surface of the hemispherical prism. The SPR light source in this and other embodiments can be configured to emit a low-coherent monochromatic light beam (e.g., 121 (FIGS. 1-5), 221 (FIG. 6), 321 (FIG. 7), or 421 (FIGS. 10-11)) for SPR imaging toward the high NA lens. The SPR camera in this and other embodiments can be configured to capture an SPR image formed after the low-coherent monochromatic light beam (e.g., 122 (FIGS. 1-5), 222 (FIG. 6), or 322 (FIG. 7)) is incident upon and reflected by a metal-coated sample contacting surface (e.g., 171 (FIG. 1-5), or 271 (FIG. 6)) of the SPR sensor. Additionally, in this and other embodiments, the high NA lens can be configured to refract the low-coherent monochromatic light beam from the SPR light source toward the hemispherical prism; and the hemispherical prism can be configured to collimate the low-coherent monochromatic light beam, as refracted by the high NA lens, toward the SPR sensor.

In another embodiment, a method for surface-plasmon-resonance (SPR) imaging can comprise: (a) coupling an SPR sensor to an optical assembly; (b) placing one or more ligand samples on a metal-coated sample contacting surface of the SPR sensor; (c) emitting a low-coherent monochromatic light beam from an SPR light source toward the high NA lens; and/or (d) capturing an SPR image by an SPR camera. In this and other embodiments, the optical assembly can comprise a hemispherical prism comprising a top surface configured to support the SPR sensor; a high numerical aperture (NA) lens; and/or a housing configured to mount the hemispherical prism and the high NA lens such that the high NA lens is located distal from the top surface of the hemispherical prism. In addition, in many embodiments, the high NA lens can be configured to refract the low-coherent monochromatic light beam from the SPR light source toward the hemispherical prism. Further, the hemispherical prism in these and other embodiments can be configured to collimate the low-coherent monochromatic light beam, as refracted by the high NA lens, toward the SPR sensor. Moreover, in these and other embodiments, the SPR image can be formed after the low-coherent monochromatic light beam is incident upon and reflected by the metal-coated sample contacting surface of the SPR sensor.

In yet another embodiment, an optical assembly for surface plasmon resonance (SPR) imaging can comprise: (a) a hemispherical prism comprising a high refractive index no less than 1.5 and a planar top surface configured to support an SPR sensor; (b) a high numerical aperture (NA) lens comprising a radius at least 1.5 times greater than a radius of the hemispherical prism; (c) a housing configured to mount the hemispherical prism and the high NA lens such that the lens is located distal from the planar top surface of the hemispherical prism; (d) a high optical resolution, not larger than 3 μm; (e) a wide SPR angle, ranging from 40 to 82 degrees; and (f) a large optical field of view, not less than 0.1 mm². In this and other embodiments, the high NA lens can be configured to refract a light toward the hemispherical prism; and/or the hemispherical prism can be configured to collimate the light, as refracted by the high NA lens, toward the SPR sensor.

Although systems and methods for SPR imaging and/or simultaneous bright light imaging have been described with reference to specific embodiments, it will be understood by those skilled in the art that various changes may be made without departing from the spirit or scope of the disclosure. Accordingly, the disclosure of embodiments is intended to be illustrative of the scope of the disclosure and is not intended to be limiting. It is intended that the scope of the disclosure shall be limited only to the extent required by the appended claims. For example, to one of ordinary skill in the art, it will be readily apparent that any components of the SPR imaging system(s) and/or optical assemblies, as well as the steps to use the SPR imaging system(s) and/or optical assemblies, may be modified, and that the foregoing discussion of certain of these embodiments does not necessarily represent a complete description of all possible embodiments.

Replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are stated in such claim.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. A system comprising:
an optical assembly comprising:
a hemispherical prism comprising a top surface configured to support a surface-plasmon-resonance (SPR) sensor;
a high numerical aperture (NA) lens; and
a housing configured to mount the hemispherical prism and the high NA lens such that the high NA lens is located distal from the top surface of the hemispherical prism;
an SPR light source configured to emit a low-coherent monochromatic light beam for SPR imaging toward the high NA lens; and
an SPR camera configured to capture an SPR image formed after the low-coherent monochromatic light beam is incident upon and reflected by a surface of the SPR sensor, wherein the surface is metal-coated and configured to contact a sample,
wherein:
the high NA lens is configured to refract the low-coherent monochromatic light beam from the SPR light source toward the hemispherical prism;
the hemispherical prism is configured to collimate the low-coherent monochromatic light beam, as refracted by the high NA lens, toward the SPR sensor; and
the high NA lens is further configured to receive and refract the low-coherent monochromatic light beam toward the SPR camera, after the low-coherent monochromatic light beam is reflected by the surface of the SPR sensor.

2. The system of claim 1, wherein the optical assembly further comprises a thermoelectric device configured to control a temperature of the SPR sensor coupled to the hemispherical prism.

3. The system of claim 1, wherein an incident angle of the low-coherent monochromatic light beam from the SPR light source towards the high NA lens is adjustable.

4. The system of claim 1 further comprising a light intensity detector configured to monitor and record an intensity of the low-coherent monochromatic light beam for intensity normalization and noise reduction.

5. The system of claim 1, wherein:
the hemispherical prism further comprises a refractive index no less than 1.5; and
the high NA lens further comprises a radius at least 1.5 times greater than a radius of the hemispherical prism.

6. The system of claim 5, wherein the optical assembly further comprises:
a high optical resolution, not larger than 3 µm;
a wide SPR angle, ranging from 40 to 82 degrees; and
a large optical field of view, not less than 0.1 mm$^2$.

7. The system of claim 1 further comprising a bright field light source and a bright field camera for bright field imaging, wherein:
the bright field light source is configured to emit a bright field light beam to illuminate the surface of the SPR sensor; and
the bright field camera is configured to capture a bright field image of the SPR sensor simultaneously with the SPR camera capturing the SPR image.

8. The system of claim 7 further comprising a phase-shift ring located between the hemispherical prism and the high NA lens and configured for phase-contrast imaging with the bright field light source and the bright field camera.

9. The system of claim 7, wherein the bright field light source and the bright field camera are further configured for fluorescence imaging with one of:
the bright field light beam emitted by the bright field light source comprising a colored light; or
the bright field light beam emitted by the bright field light source comprising a white light and a color filter located at one of: between the bright field light source and the SPR sensor or in front of the bright field camera, the color filter configured to change one or more colors of the bright field light beam.

10. The system of claim 7, wherein:
the SPR camera and the bright field camera are communicably coupled to a computing system;
the SPR camera is further configured to transmit the SPR image to the computing system;
the bright field camera is further configured to transmit the bright field image to the computing system; and
the computing system is configured to:
receive and record the SPR image transmitted from the SPR camera;
receive and record the bright field image transmitted from the bright field camera;
calibrate the SPR image received from the SPR camera;
calibrate the bright field image received from the bright field camera; and
map the SPR image onto the bright field image for binding analysis.

11. A method for surface-plasmon-resonance (SPR) imaging comprising:
coupling an SPR sensor to an optical assembly, the optical assembly comprising:
a hemispherical prism comprising a top surface configured to support the SPR sensor;
a high numerical aperture (NA) lens; and
a housing configured to mount the hemispherical prism and the high NA lens such that the high NA lens is located distal from the top surface of the hemispherical prism;
placing one or more ligand samples on a surface of the SPR sensor, wherein the surface is metal-coated;
emitting a low-coherent monochromatic light beam from an SPR light source toward the high NA lens; and
capturing an SPR image by an SPR camera, wherein:
the high NA lens is configured to refract the low-coherent monochromatic light beam from the SPR light source toward the hemispherical prism;
the hemispherical prism is configured to collimate the low-coherent monochromatic light beam, as refracted by the high NA lens, toward the SPR sensor;
the SPR image is formed after the low-coherent monochromatic light beam is incident upon and reflected by the surface of the SPR sensor; and
the high NA lens is further configured to receive and refract the low-coherent monochromatic light beam toward the SPR camera, after the low-coherent monochromatic light beam is reflected by the surface of the SPR sensor.

12. The method of claim 11, wherein the optical assembly further comprises a thermoelectric device configured to control a temperature of the SPR sensor coupled to the hemispherical prism.

13. The method of claim 11 further comprising adjusting an incident angle of the low-coherent monochromatic light beam from the SPR light source towards the high NA lens to allow scanning an SPR angle profile and to optimize a detection sensitivity.

14. The method of claim 11 further comprising providing a light intensity detector for intensity normalization and noise reduction, the light intensity detector configured to monitor and record an intensity of the low-coherent monochromatic light beam.

15. The method of claim 11, wherein:
the hemispherical prism further comprises a refractive index no less than 1.5; and
the high NA lens further comprises a radius at least 1.5 times greater than a radius of the hemispherical prism.

16. The method of claim 15, wherein the optical assembly further comprises:
a high optical resolution, not larger than 3 µm;
a wide SPR angle, ranging from 40 to 82 degrees; and
a large optical field of view, not less than 0.1 mm².

17. The method of claim 11 further comprising:
emitting a bright field light beam from a bright field light source to illuminate the surface of the SPR sensor; and
capturing a bright field image of the SPR sensor by a bright field camera simultaneously with capturing the SPR image by the SPR camera.

18. The method of claim 17 further comprising:
placing a phase-shift ring between the hemispherical prism and the high NA lens and configured for phase-contrast imaging with the bright field light source and the bright field camera.

19. The method of claim 17, wherein the bright field light source and the bright field camera are further configured for fluorescence imaging with one of:
changing a color of the bright field light beam emitted by the bright field light source; or
placing a color filter at one of: between the bright field light source and the SPR sensor or in front of the bright field camera, the color filter configured to change one or more colors of the bright field light beam.

20. The method of claim 17 further comprising:
transmitting the SPR image from the SPR camera to a computing system; and
transmitting the bright field image from the bright field camera to the computing system, wherein:
the computing system is configured to:
receive and record the SPR image transmitted from the SPR camera;
receive and record the bright field image transmitted from the bright field camera;
calibrate the SPR image received from the SPR camera;
calibrate the bright field image received from the bright field camera; and
map the SPR image onto the bright field image for binding analysis.

21. An optical assembly for surface plasmon resonance (SPR) imaging comprising:
a hemispherical prism comprising a high refractive index no less than 1.5 and a top surface configured to support an SPR sensor;
a high numerical aperture (NA) lens comprising a radius at least 1.5 times greater than a radius of the hemispherical prism;
a housing configured to mount the hemispherical prism and the high NA lens such that the high NA lens is located distal from the top surface of the hemispherical prism;
a high optical resolution, not larger than 3 µm;
a wide SPR angle, ranging from 40 to 82 degrees; and
a large optical field of view, not less than 0.1 mm²,
wherein:
the high NA lens is configured to refract a light toward the hemispherical prism;
the hemispherical prism is configured to: (a) collimate the light, as refracted by the high NA lens, toward the SPR sensor, and (b) receive and refract the light, reflected by the SPR sensor, toward the high NA lens; and
the high NA lens is further configured to receive the light, as refracted from the hemispherical prism.

22. The optical assembly of claim 21 further comprising a thermoelectric device configured to control a temperature of the SPR sensor coupled to the hemispherical prism.

* * * * *